(12) United States Patent
Grasruck et al.

(10) Patent No.: US 9,931,088 B2
(45) Date of Patent: Apr. 3, 2018

(54) DISPLAYING AN ACQUISITION FIELD OF VIEW

(71) Applicant: Siemens Aktiengesellschaft, Munich (DE)

(72) Inventors: Michael Grasruck, Nuernberg (DE); Bernhard Krauss, Burgthann (DE); Martin Sedlmair, Zirndorf (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 268 days.

(21) Appl. No.: 14/566,829

(22) Filed: Dec. 11, 2014

(65) Prior Publication Data

US 2015/0164444 A1   Jun. 18, 2015

(30) Foreign Application Priority Data

Dec. 17, 2013 (DE) .......................... 10 2013 226 238

(51) Int. Cl.
   *A61B 6/08* (2006.01)
   *A61B 6/03* (2006.01)
(52) U.S. Cl.
   CPC ................ *A61B 6/08* (2013.01); *A61B 6/032* (2013.01)
(58) Field of Classification Search
   CPC . A61B 6/032; A61N 5/1049; A61N 2005/105
   See application file for complete search history.

(56) References Cited

U.S. PATENT DOCUMENTS

| | | | |
|---|---|---|---|
| 4,502,147 A * | 2/1985 | Michaels ................. | A61B 6/08 378/150 |
| 5,080,100 A | 1/1992 | Trotel | |
| 5,188,110 A | 2/1993 | Sugimoto | |
| 5,684,854 A | 11/1997 | Hughes | |
| 6,041,249 A * | 3/2000 | Regn ........................ | A61B 6/08 378/20 |

(Continued)

FOREIGN PATENT DOCUMENTS

| | | |
|---|---|---|
| CN | 1176143 A | 3/1998 |
| CN | 1980605 A | 6/2007 |

(Continued)

OTHER PUBLICATIONS

Sedlmair Martin: "Direkte Übertragung von Informationen für interventionelle Untersuchungen auf den Patienten durch ein Laserarray", in: Technik Report, vol. 99, pp. 1-3; Jul. 23, 2009 and English translation.

(Continued)

*Primary Examiner* — Hoon Song
(74) *Attorney, Agent, or Firm* — Harness, Dickey & Pierce, P.L.C.

(57) ABSTRACT

A method is disclosed for displaying a selected acquisition field of view of a medical tomography apparatus in the region of a patient table of the tomography apparatus with the aid of an illumination device including at least one light source. In this regard, the illumination device includes at least one setting device for revealing and/or masking boundary areas of a field of illumination of the illumination device which are revealed or masked as a function of the selected acquisition field of view. An illumination device is also disclosed for this purpose.

19 Claims, 3 Drawing Sheets

(56) References Cited

U.S. PATENT DOCUMENTS

| | | | |
|---|---|---|---|
| 8,005,187 B2* | 8/2011 | Suzuki | A61B 6/032 378/19 |
| 2007/0030957 A1* | 2/2007 | Pommi | A61B 6/469 378/197 |
| 2007/0183565 A1 | 8/2007 | Brandstatter et al. | |
| 2009/0046252 A1 | 2/2009 | Heym et al. | |
| 2010/0208274 A1* | 8/2010 | Kindlein | A61B 6/08 356/603 |
| 2012/0220863 A1 | 8/2012 | Hannemann | |

FOREIGN PATENT DOCUMENTS

| | | |
|---|---|---|
| DE | 10324072 B4 | 9/2007 |
| DE | 102008061454 A1 | 4/2010 |
| DE | 102011004747 A1 | 8/2012 |
| JP | 2006122479 A | 5/2006 |

OTHER PUBLICATIONS

Dr. Sedlmair Martin: "Nadelpositionierung and Steuerung", in: Journal Technik Up2date2010#09, pp. 60-61, ISSN: 2190-2399: Aug. 20, 2010 and English translation.
German Office Action dated Aug. 20, 2014.
Office Action for Chinese Patent Application No. 201410785599.4 dated Jun. 20, 2017 and English translation thereof.
Office Action for Chinese Patent Application No. 201410785599.4 dated Oct. 28, 2016 and English translation thereof.
Office Action for Chinese Patent Application No. 201410785599.4 dated Nov. 1, 2017 and English translation thereof.

* cited by examiner

DISPLAYING AN ACQUISITION FIELD OF VIEW

PRIORITY STATEMENT

The present application hereby claims priority under 35 U.S.C. § 119 to German patent application number DE 102013226238.8 filed Dec. 17, 2013, the entire contents of which are hereby incorporated herein by reference.

FIELD

At least one embodiment of the present invention generally relates to a method for displaying a selected acquisition field of view of a medical tomography apparatus in the region of a patient table of the tomography apparatus with the aid of an illumination device comprising at least one light source. At least one embodiment of the invention furthermore relates to an illumination device for displaying a selected acquisition field of view of a medical tomography apparatus in the region of a patient table of the tomography apparatus.

BACKGROUND

The term medical tomography apparatus encompasses, for example, computed tomography (CT) scanners, magnetic resonance (MR) tomography scanners, angiography scanners, single proton emission computed tomography (SPECT) scanners and positron emission tomography (PET) scanners.

In planning the acquisition of tomographic images by means of a medical tomography apparatus, use is often made of topograms. As a preliminary step in a CT imaging session, a topogram scan is performed in such a way that the topogram, i.e. the overview image, is recorded at a specific angle (for example, anterior-posterior or lateral) with a stationary X-ray source and stationary detector arrangement and—compared to the subsequent actual CT scan which leads to the acquisition of images suitable for diagnostic findings—at a lower radiation dose. The positioning of the examination object, i.e. the patient, for example, on the patient table of the tomography apparatus is carried out in this case such that the examination object is placed onto the patient table.

In order to indicate the start position of the topogram scan (and/or of the ensuing imaging scan) for the user (i.e. the radiologist or radiological technician), a marking can be made by means of a laser marker integrated into the tomography apparatus. Such a solution is disclosed for example in the German patent application DE 10 2011 004 747 A1. A fixed length of the topogram scan can be set on the operator console of the tomography apparatus and the scan can be performed. Optionally, the topogram scan can be terminated prematurely by pressing a stop button in order to reduce the radiation dose to a minimum.

The problem resulting from this method of proceeding is that only the start position of the (topogram) scan is visualized by way of the laser marking in the region of the patient table, but not the end position of the acquisition field of view. Even if a further marking laser were to be available, a further problem would exist in that the setting of the acquisition field of view is carried out only from the control room, since the options for operator control of the tomography system in the actual examination room are very limited. As a consequence the end position of the topogram can only be set by the user's moving back and forth several times from the examination room to the control room, which significantly complicates the clinical workflow. Furthermore, the laser marking is carried out in the examination region of the tomography apparatus, i.e. inside the so-called gantry, in other words at the place where the images are subsequently acquired: This is because that is where the marking laser is located. This necessitates moving the examination object into the gantry, thereby greatly restricting the user's field of vision at the same time, which makes it considerably more difficult to achieve an optimal setting of the acquisition field of view.

The article by Martin Sedlmair titled "Nadelpositionierung and Steuerung" ("Needle positioning and control") in the journal Technik Up2date 2010 No. 9, pp. 60 to 61, proposes using an LCD video projector for projecting anatomies onto a patient on a patient table of a tomography system. However, this solution is associated with a relatively high level of technical complexity and financial outlay, and in addition, due to the typically relatively low light output of LCD video projectors, is only suitable to a limited degree for displaying an acquisition field of view. If, on the other hand, a high light output is set, there is the risk of dazzling the patient and/or user, so that protective glasses for user and patient might even have to be used, which overall entails a negative intrusion into the clinical workflow.

SUMMARY

At least one embodiment of the present invention is directed to an illumination device and/or method for displaying an acquisition field of view of a medical imaging of a medical tomography apparatus.

A method and an illumination device are disclosed.

In an embodiment of the method, the illumination device has one or more setting devices for revealing and/or masking boundary areas of a field of illumination of the illumination device, which boundary areas are revealed or masked as a function of the selected acquisition field of view.

An inventive illumination device of an embodiment includes an interface to the tomography apparatus, at least one light source, and at least one setting device for revealing and/or masking boundary areas of a field of illumination of the illumination device, which boundary areas can be revealed or masked as a function of the selected acquisition field of view. The illumination device can therefore be used for performing the method according to an embodiment of the invention.

In addition, at least one embodiment of the invention therefore also relates to the use of an inventive illumination device for displaying a selected acquisition field of view of a medical tomography apparatus in the region of a patient table of the tomography apparatus.

At least one embodiment of the invention furthermore relates to a medical system comprising a medical tomography apparatus having an acquisition unit as well as an inventive illumination device.

The execution sequence of the method according to at least one embodiment of the invention particularly preferably comprises:

selecting an acquisition field of view by way of the illumination device and/or via a control interface of the tomography apparatus, optionally: synchronizing data relating to the currently selected acquisition field of view between the illumination device and the tomography apparatus, displaying the selected acquisition field of view in the region of the patient table of the tomography apparatus with the aid of the illumination device, and moving the patient table into an acquisition unit of the tomography apparatus for the purpose of image acquisition (i.e. including, for example, topogram acquisition) in the selected acquisition field of view.

BRIEF DESCRIPTION OF THE DRAWINGS

The invention is explained once again in more detail hereinbelow with the aid of example embodiments and with reference to the attached figures. In the various figures, like components are provided with identical reference numerals. In the figures.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

An inventive illumination device of an embodiment includes an interface to the tomography apparatus, at least one light source, and at least one setting device for revealing and/or masking boundary areas of a field of illumination of the illumination device, which boundary areas can be revealed or masked as a function of the selected acquisition field of view. The illumination device can therefore be used for performing the method according to an embodiment of the invention.

In this case the illumination device preferably emits light at least also in the visible light wavelength range, i.e. the light source itself generates such light and/or other parts of the illumination device convert light of the light source into such in the visible light wavelength range.

The region of the patient table is defined in particular as that spatial domain which lies above the patient table, i.e. which is defined by a vertical projection of the patient table upward to above the patient table. In this context "above" the patient table is on the side of the patient table where the examination object, i.e. a patient for example, is also positioned in accordance with the intended purpose. The region of the patient table can be demarcated in particular from the field of examination of the tomography system, i.e. an interior space, for instance inside a gantry, of the tomography system, in which the patient is ordinarily situated only for imaging purposes.

With the aid of an embodiment of the (inventive) illumination device, it is possible by use of the setting device to display the currently set acquisition field of view of a planned tomography scan (i.e. both of a topogram scan and of an imaging scan according to the above definition) in a targeted manner such that it is directly and precisely illuminated with the light of the light source. What is achieved by use of the setting device in this case is that the light is displayed in the acquisition field of view on the patient table or the patient, while regions that are not to be scanned remain unlit. The setting devices differ from a lens of a video projector to the extent that they can reveal and mask the respective boundary areas of the acquisition field of view in a targeted manner. In other words, a focus setting is not necessarily varied, but rather there is simply an active revealing and masking of the light-emitting surface of the illumination device. As a result it is possible to avoid dazzling users and patients in a targeted manner and a strong illuminating power of the illumination device can be used nonetheless.

An inventive illumination device of an embodiment includes an interface to the tomography apparatus, at least one light source, and at least one setting device for revealing and/or masking boundary areas of a field of illumination of the illumination device, which boundary areas can be revealed or masked as a function of the selected acquisition field of view. The illumination device can therefore be used for performing the method according to an embodiment of the invention.

In addition, at least one embodiment of the invention therefore also relates to the use of an inventive illumination device for displaying a selected acquisition field of view of a medical tomography apparatus in the region of a patient table of the tomography apparatus.

At least one embodiment of the invention furthermore relates to a medical system comprising a medical tomography apparatus having an acquisition unit as well as an inventive illumination device.

Further particularly advantageous embodiments and developments of the invention will also become apparent from the dependent claims as well as from the following description. In this regard the illumination device can also be developed in accordance with the respective dependent claims relating to the method.

Preferably the setting devices reveal or mask the boundary areas substantially along a z-direction and/or a y-direction of the tomography apparatus. In this way the acquisition field of view is therefore displayed such that it is limited in the longitudinal extension of the patient table and/or in the latter's lateral extension—preferably both—by the setting devices.

The illumination device can advantageously comprise a light box enclosing the light source in a substantially light-tight manner and having a light transmission aperture. During the operation of the illumination device, light is then emitted through the light transmission aperture in the direction of the patient table. The substantially light-tight enclosing by means of the light box serves in particular to prevent the occurrence of any disturbance factors caused by light from the illumination device, for example the above-described dazzling effects for user or patient. Such an enclosure is therefore particularly advantageous practically independently of the light source in the performance of the method according to an embodiment of the invention.

In an advantageous development of the invention, it is provided that between the at least one light source and the patient table the illumination device comprises an at least partially translucent, in particular preferably a substantially (i.e. over the majority of its surface) transparent projection disk. The projection disk has supplementary information which is preferably predefined and particularly preferably permanently impressed on the projection disk. The supplementary information is then projected with the aid of light from the light source—in a similar way to a slide or overhead projector—in the direction of the patient table. Such supplementary information can include for example written information or symbols, for instance pictograms or characters or dimensions (such as a schematic ruler).

By this, it is possible for example to indicate schematically the location of organs of the patient (and/or of a patient ideal type) or the scan direction or, as the case may be, the patient position that is to be set, etc., by projection onto the patient table or patient. Such a projection disk can be embodied for example as a rotary disk which is rotated in each case in front of the light source in such a way that the desired supplementary information is projected.

Preferably the setting devices comprise at least one shutter, the setting of which is varied as a function of the selected acquisition field of view. Moving the shutter in its direction of opening accordingly causes the acquisition field of view displayed at the patient table to be increased in size, while movement in the opposite direction produces a reduction in its size. In this case the shutter can be embodied in particular as part of a light box of the illumination device. Using a number of shutters as setting means constitutes a simple yet nonetheless effective measure for enabling the display of the acquisition field of view to be varied. In particular the shutters can even be set manually, thereby resulting in two basic handling options, though these can also combined with one another.

The first option is to set or vary the acquisition field of view on the tomography apparatus, in particular on a control unit of the tomography apparatus, and to adapt the shutter setting of the illumination device accordingly by automatic command transmission to an actuator which implements the shutter setting.

The second option is that the user carries out the shutter setting in the examination room and that corresponding sensors determine said shutter setting and forward it to the tomography apparatus. The tomography apparatus then sets the acquisition field of view internally according to the selected shutter setting.

Both options can also be used in a complementary manner, i.e. the user has the choice of at which interface —shutter or control unit—to set or select the acquisition field of view.

It is generally preferred that the illumination device is embodied in such a way that it emits light of substantially the same light intensity and/or same colorimetric locus over the entire field of illumination. The illumination device therefore comprises a number of homogeneous light sources (which, in the case of a plurality of light sources, are homogeneously coordinated with one another) and/or it has a focusing screen or other type of optical filter and/or focusing device which ensures such a uniform, i.e. homogeneous emission. By this means the patient table is correspondingly homogeneously illuminated, so that the boundaries of the selected acquisition field of view are clearly recognizable to the user.

As far as the light source is concerned, various embodiment options exist. A first such embodiment option provides that the light source comprises a tubular lamp whose light is emitted in the direction of the patient table. Included within the definition of tubular lamps are all those lamps which are enclosed in a glass or glass-like tube, such as, say, the traditional incandescent lamp, but also gas discharge lamps. Particularly preferred are such tubular lamps which give off a substantially homogeneous light spectrum.

In this instance, but also quite generally within the scope of the invention, light emitted by the light source can advantageously be deflected by way of a mirror and/or lens system of the illumination device, its light beams preferably being parallelized and/or focused. By way of the deflection, the direction of the light emitted by the illumination device in the direction of the patient table can be set such that for example shadow formations at the boundaries of the acquisition field of view can be excluded to the greatest possible extent. This is achieved in particular by way of parallelized light.

A second embodiment option of the light source provides that the light source comprises a planar light emitter which is actuated in such a way that substantially exclusively the selected acquisition field of view is illuminated by the planar light emitter. Examples of embodiments of planar light emitters are explained hereinbelow. A common feature they share is that preferably they can be actuated selectively, which means that the above-described use of shutters is not absolutely necessary here. Similarly, an enclosing light box can also be dispensed in principle (though not necessarily) in this case.

Planar light emitters have a light-emitting surface instead of a spiral-wound filament or an illumination volume. The light-emitting surface can also be realized by irradiation from punctiform and/or linear or illumination-volume-based individual sources from behind or by projection onto a radiating surface, in which case the radiating surface then directs the light in the direction of the patient table.

One example of a preferred planar light emitter is that the planar light emitter comprises an electroluminescent lamp which is actuated segment by segment. Such an electroluminescent lamp can be realized as an electroluminescent film or else as a thicker flat electroluminescent structure. It can be embodied either as an organic electroluminescent lamp or as an inorganic electroluminescent lamp. In organic electroluminescent lamps, a current is conducted in one direction through an organic pigment layer over the surface area by way of electrodes (which can be segmented in the relevant area) applied to both sides of the pigment layer, the current exciting the pigment layer into illumination.

In inorganic electroluminescent lamps, in contrast, no current flows, but rather an alternating electric field is applied to both sides of the pigment layer, the field again exciting the pigment layer into illumination. Electroluminescent lamps are therefore systems particularly well-suited to the purpose generally within the scope of the invention, because they generate little to no heat when emitting light and can be readily actuated segment by segment by way of a corresponding converter.

A second example of another preferred planar light emitter is that the planar light emitter comprises a plurality of light sources substantially in one surface area, the light sources being selectively actuated individually or in groups. The light of such a plurality of light sources can then be emitted, for example by way of a focusing screen (where appropriate, also subdivided into segments), in the direction of the patient table. Particularly preferably the light sources are individual LEDs. The light sources can for example be arranged in a light source array, for example in the form of a matrix, and/or uniformly distributed according to a predetermined pattern. Various optical elements such as diffusors, lenses, mirrors, focusing screens, etc. can be used as complementary to the light sources. The advantages of this type of planar light emitter are substantially analogous to those of electroluminescent lamps in that they too can be actuated for example effectively segment by segment.

The embodiment options for light sources outlined above can also be combined with one another, for instance by combination of an electroluminescent lamp with an incandescent lamp, etc.

The execution sequence of the method according to at least one embodiment of the invention particularly preferably comprises:
 selecting an acquisition field of view by way of the illumination device and/or via a control interface of the tomography apparatus,
 optionally: synchronizing data relating to the currently selected acquisition field of view between the illumination device and the tomography apparatus,
 displaying the selected acquisition field of view in the region of the patient table of the tomography apparatus with the aid of the illumination device, and
 moving the patient table into an acquisition unit of the tomography apparatus for the purpose of image acquisition (i.e. including, for example, topogram acquisition) in the selected acquisition field of view.

Figure 1:
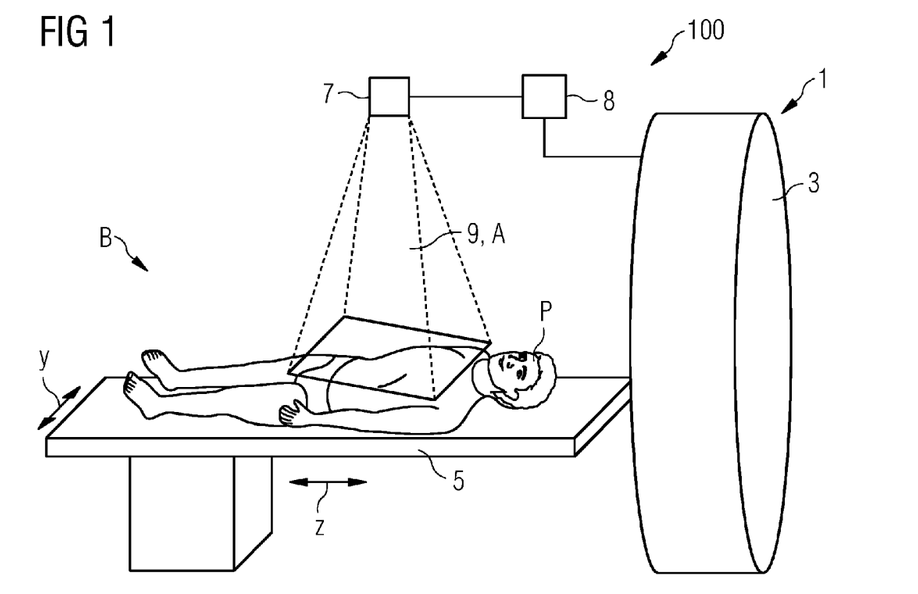
FIG. 1 shows a side view of an example embodiment of a medical system according to the invention.

FIG. 1 shows a medical system 100 comprising an illumination device 7 according to an embodiment of the invention and a medical tomography apparatus 1, in this case a CT scanner 1. The patient table 5 and an acquisition unit 3 for image acquisition are shown here as parts of the tomography apparatus 1. The illumination device 7 includes an interface 8 to the tomography apparatus 1.

The patient table 5 together with an examination object P positioned thereon, in this case a patient P, can be moved into the interior zone of the acquisition unit by displacement in the z-direction z. The second substantially horizontal direction of the patient table in addition to the z-direction is the y-direction, which lies at right angles to the z-direction.

A light beam is directed in a field of illumination 9 by way of the illumination device 7 into the region B of the patient table 5, i.e. from above onto the patient table 5 and consequently also onto the patient P. At the point where it is incident on the patient P or the patient table 5—in particular in the y- and z-direction—the field of illumination 9 defines a currently set acquisition field of view A of the tomography apparatus 1. Changing the acquisition field of view A automatically also causes the field of illumination 9 to be changed accordingly, and/or vice versa.

FIGS. 2 to 6 show different possible example embodiments of illumination devices according to the invention which can be used for example within the framework of the medical system just described.

Figure 2:
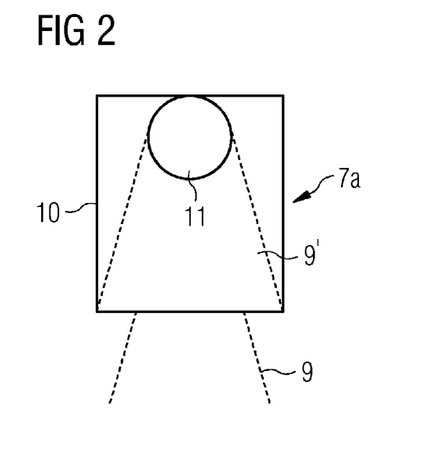
FIG. 2 shows a sectional view of a first example embodiment of an illumination device according to the invention.

FIG. 2 shows an illumination device 7a according to an embodiment of the invention having a light source 11 in the form of a tubular lamp 11 represented here schematically. The light source 11 is enclosed in a substantially light-tight manner in a light box 10 which is open at the bottom (not shown), the opening of the light box 10 being variable so that of the light 9' originally transmitted by the light source 11 only the desired field of illumination 9 is emitted in the direction of the patient table 5 by the illumination device 7a.

Figure 3:
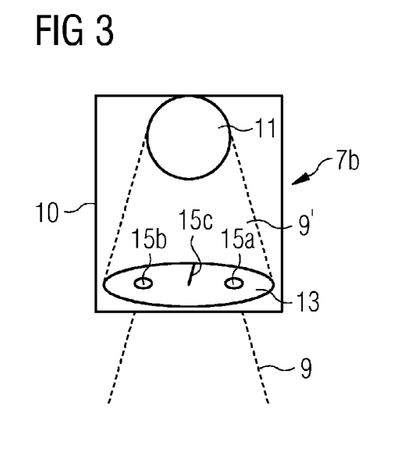
FIG. 3 shows a sectional view of a second example embodiment of an illumination device according to the invention.

The illumination device 7b, which essentially represents a development of the illumination device 7a shown in FIG. 2, is also to be seen analogously hereto. Like reference signs are therefore not explained separately a second time. Installed in addition in this case inside the light box 10 on the opening side is a substantially transparent projection disk 13 (shown perspectively here for illustration purposes), which is embodied as a rotary disk 13. Superimposed on the projection disk 13 are a plurality of symbols 15a, 15b, 15c which can be projected onto the patient P or the patient table 5 by means of the light spilling out from the illumination device 7b. The symbols can include for example direction and/or marking symbols.

Figure 4:
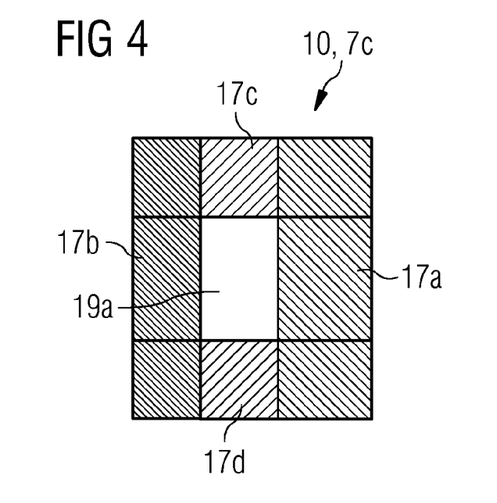
FIG. 4 shows a view from below onto a third example embodiment of an illumination device according to the invention.

FIG. 4 shows a bottom view of an illumination device 7c according to an embodiment of the invention, i.e. a view onto the underside of a light box 10 of the illumination device 7c. The illumination device 7c comprises four movable shutters 17a, 17b, 17c, 17d, wherein given proper mounting and alignment of the illumination device 7c the inner boundaries of the shutters 17a, 17b, 17c, 17d are aligned in each case parallel to the z-direction or to the y-direction of the corresponding tomography apparatus. As a result of at least one of the two side shutters 17a, 17b and/or at least one of the shutters 17c, 17d, shown here at top and bottom, being shifted inward, i.e. in the direction of the center of the light outlet aperture 19a, the light outlet aperture 19a is reduced in size, whereas in the reverse case it is increased in size. This enables the field of illumination 9 of the illumination device to be adjusted, since the light outlet aperture 19a forms the (planar) emission region 19a which defines the field of illumination 9.

Figure 5:
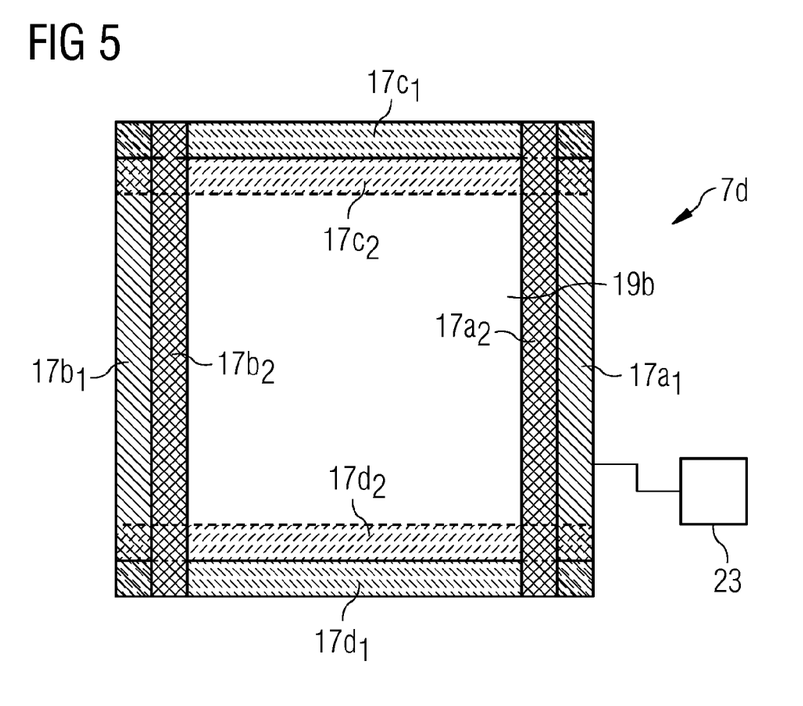
FIG. 5 shows a view from below onto a fourth example embodiment of an illumination device according to the invention.

FIG. 5 shows as light source 7d and illumination device 7d an electroluminescent lamp 7d which is controlled with the aid of a converter 23 as a function of the selected acquisition field of view. The electroluminescent lamp 7d is subdivided into segments, only two activatable and deactivatable (i.e. which can be illuminated or are not illuminated) segment sections 17a1, 17a2, 17b1, 17b2, 17c1, 17c2, 17d1, 17d2 being shown here for clarity of illustration reasons both on the top and bottom and on both sides to left and right: Analogously to the displacement of the shutters 17a, 17b, 17c, 17d in FIG. 4, the emission region 19b of the electroluminescent lamp 7d can be set in this case by way of the converter 23 by activation or deactivation of said segment sections 17a1, 17a2, 17b1, 17b2, 17c1, 17c2, 17d1, 17d2 as a function of the selected acquisition field of view A. Accordingly, the converter 23, together with the individually actuatable segment sections 17a1, 17a2, 17b1, 17b2, 17c1, 17c2, 17d1, 17d2, is to be understood as setting devices within the meaning of embodiments of the invention.

Figure 6:
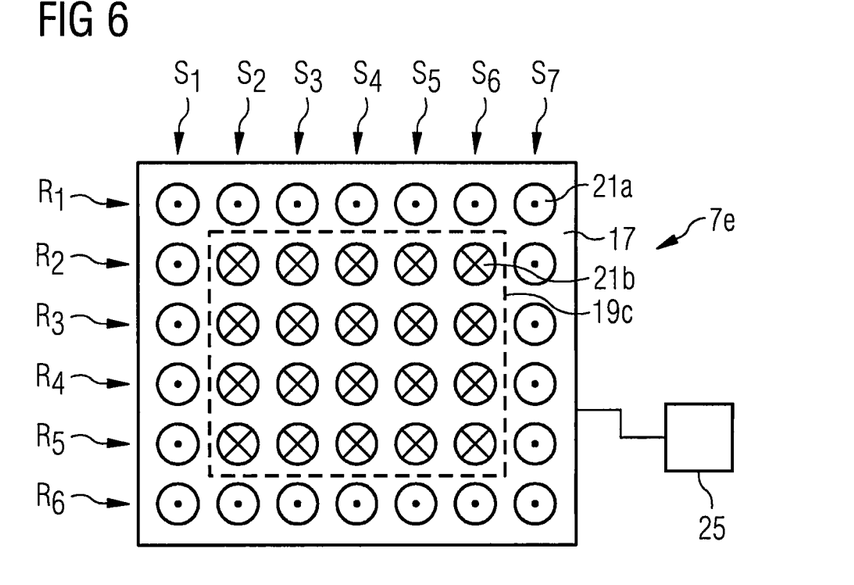
FIG. 6 shows a view from below onto a fifth example embodiment of an illumination device according to the invention.

The last example embodiment of an illumination device 7e according to the invention selected here in the form of a matrix-like LED array 7e arranged behind a focusing screen (not shown) can also be understood analogously, which LED array 7e can likewise be adjusted by way of a control unit 25 in analogy to the converter 23 just mentioned. Individual LEDs 21a, 21b, ... are arranged here in rows $R_1, R_2, R_3, R_4, R_5, R_6$ and columns $S_1, S_2, S_3, S_4, S_5, S_6, S_7$, and each can be switched on and off individually by way of the control unit 25. In the state schematically shown here, all LEDs 21a in a dark section 17 are switched off. These are all LEDs 21a in the topmost and bottommost row $R_1, R_6$ as well as in the leftmost and rightmost column $S_1, S_7$. All other LEDs 21b are switched on and accordingly form the emission region 19c of the illumination device 7e. The dimensions and distribution of said emission region 19c are specified by the control unit 25 once again as a function of the selected acquisition field of view A of the tomography apparatus 1.

Figure 7:
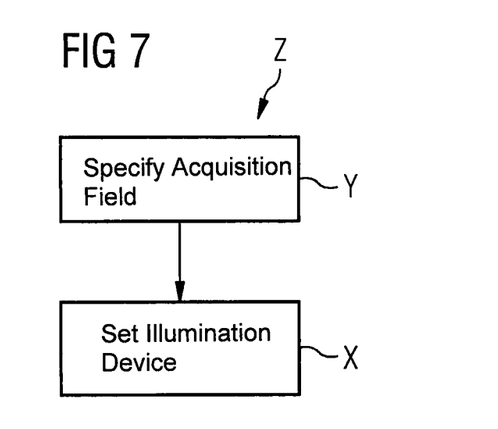
FIG. 7 is a schematic block diagram illustrating the execution sequence of an example embodiment of the method according to the invention.

FIG. 7 schematically shows two steps of an example embodiment of the method according to the invention Z for displaying a selected acquisition field of view A of a medical tomography apparatus 1 in the region B of a patient table 5 of the tomography apparatus 1 with the aid of an illumination device 7, 7a, 7b, 7c, 7d, 7e according to the invention. Initially, in a first step Y, said acquisition field of view A is or has been specified or is varied. In a second step X, the illumination device 7, 7a, 7b, 7c, 7d, 7e is then set with the aid of setting means 17a, 17b, 17c, 17d, 23, 25 such that boundary areas of a field of illumination 9 of the illumination device 7, 7a, 7b, 7c, 7d, 7e are revealed or masked as a function of the selected acquisition field of view A.

In conclusion it is pointed out once again that the method described in detail hereinabove and the devices presented are merely example embodiments which can be modified in the most diverse ways by the person skilled in the art without leaving the scope of the invention. Furthermore, the use of the indefinite article "a" or "an" does not exclude the possibility that the features in question may also be present more than once.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for displaying a selected acquisition field of view of a medical tomography apparatus in the region of a patient table of the tomography apparatus with the aid of an illumination device including at least one light source located outside of the medical tomography apparatus, the method comprising:
    selecting an acquisition field of view by illuminating only the region of the patient table to be scanned by the medical tomography apparatus via the illumination device located outside of the medical tomography apparatus with light in the visible light wavelength range, the region being located outside of an image acquisition device of the tomography apparatus; and
    at least one of revealing and masking boundary areas of a field of illumination of the illumination device via setting devices of the illumination device, the boundary areas being at least one of revealed and masked as a function of the selected acquisition field of view, wherein, between the at least one light source and the patient table, the illumination device includes projection disk therein that is transparent over a majority of its surface, the projection disk including non-transparent supplementary information which is projectable with the aid of visible light from the light source in the direction of the patient table.

2. The method of claim 1, wherein the setting devices at least one of reveal and mask the boundary areas substantially along at least one of a z-direction and a y-direction of the tomography apparatus.

3. The method of claim 1, wherein the illumination device includes a light box, enclosing the light source in a substantially light-tight manner, including a light transmission aperture, light being emitted through the light transmission aperture in the direction of the patient table during the operation of the illumination device.

4. The method of claim 1, wherein the setting devices comprise at least one shutter, the setting of which is variable as a function of the selected acquisition field of view.

5. The method of claim 1, wherein the illumination device is embodied in such a way to emit light of at least one of substantially the same light intensity and same colorimetric locus over the entire field of illumination.

6. The method of claim 1, wherein the light source comprises a tubular lamp whose light is emitted in the direction of the patient table.

7. The method of claim 1, wherein light emitted by the light source is deflected by way of at least one of a mirror and lens system of the illumination device.

8. The method of claim 1, wherein the light source comprises a planar light emitter, actuated such that substantially exclusively, the selected acquisition field of view is illuminated by the planar light emitter.

9. The method of claim 8, wherein the planar light emitter comprises an electroluminescent lamp, actuated segment by segment.

10. The method of claim 8, wherein the planar light emitter comprises a plurality of light sources substantially in one surface area, wherein the light sources are selectively actuated individually or in groups.

11. The method of claim 1, further comprising:
    a control interface of the tomography apparatus configured to change the acquisition field of view in accordance with a change in the illuminated region;
    displaying the selected acquisition field of view in the region of the patient table of the tomography apparatus with the aid of the illumination device; and
    moving the patient table into image acquisition device of the tomography apparatus for the purpose of image acquisition in the selected acquisition field of view.

12. An illumination device for displaying a selected acquisition field of view of a medical tomography apparatus in a region of a patient table of the tomography apparatus, comprising:
    an interface to the tomography apparatus configured to change the acquisition field of view in accordance with a change in an illuminated region of the patient table;
    at least one light source, that provides light in the visible light wavelength range, located outside of an interior space of the tomography apparatus; and
    at least one setting device for at least one of revealing and masking boundary areas of a field of illumination of the illumination device, the boundary areas being at least one of revealable and maskable as a function of the selected acquisition field of view, wherein, between the at least one light source and the patient table, the illumination device includes projection disk therein that is transparent over a majority of its surface, the projection disk including non-transparent supplementary information which is projectable with the aid of visible light from the light source in the direction of the patient table.

13. A method, comprising:
    using the illumination device of claim 12 for displaying a selected acquisition field of view of a medical tomography apparatus in the region of a patient table of the tomography apparatus.

14. A medical system, comprising:
    a medical tomography apparatus including an image acquisition device and the illumination device of claim 12.

15. The method of claim 2, wherein the illumination device includes a light box, enclosing the light source in a substantially light-tight manner, including a light transmission aperture, light being emitted through the light transmission aperture in the direction of the patient table during the operation of the illumination device.

16. The method of claim 7, wherein light beams of the light are at least one of parallelized and focused.

17. The method of claim 11, further comprising:
    synchronizing data relating to the currently selected acquisition field of view between the illumination device and the tomography apparatus.

18. The method of claim 1, wherein selecting the acquisition field of view includes emitting the visible light through supplementary information on the projection disk that is permanently impressed on the projection disk and the supplementary information includes at least one of written information or symbols.

19. The illumination device of claim 12, wherein the projection disk includes supplementary information that is permanently impressed on the projection disk and the supplementary information includes at least one of written information or symbols.

* * * * *